United States Patent [19]

Sculthorpe

[11] Patent Number: 4,483,838

[45] Date of Patent: Nov. 20, 1984

[54] TREATMENT OF CONTAMINATED PHOSPHORIC ACID TO RECOVER USABLE ACID THEREFROM

[75] Inventor: Donald L. Sculthorpe, Las Vegas, Nev.

[73] Assignee: Stauffer Chemical Company, Westport, Conn.

[21] Appl. No.: 534,421

[22] Filed: Sep. 21, 1983

[51] Int. Cl.$^3$ ............................................. C01B 25/16
[52] U.S. Cl. ................................ 423/321 R; 423/316; 423/317
[58] Field of Search ............... 423/316, 317, 319, 320, 423/321 R, 525, 528; 568/65

[56] References Cited

U.S. PATENT DOCUMENTS

| | | | |
|---|---|---|---|
| 2,345,506 | 3/1944 | Slotterbeck | 423/528 |
| 2,947,788 | 8/1960 | Pitt | 568/65 |
| 3,734,699 | 5/1973 | Pitt | 568/65 |
| 4,256,721 | 3/1981 | Blakey et al. | 423/525 |
| 4,415,506 | 11/1983 | Carron, et al. | 260/986 |

*Primary Examiner*—Gregory A. Hewer
*Attorney, Agent, or Firm*—Joel G. Ackerman

[57] ABSTRACT

Phosphoric acid containing organic contaminants, such as phosphoric acid recovered from a thiophenol process, is treated to recover usable acid by conducting a hot separation of the contaminated acid into acidic and organic phases, removing the organic phase, preheating the acidic phase, stripping the latter with steam and removing any remaining organic contaminants from the stripped acid.

8 Claims, 1 Drawing Figure

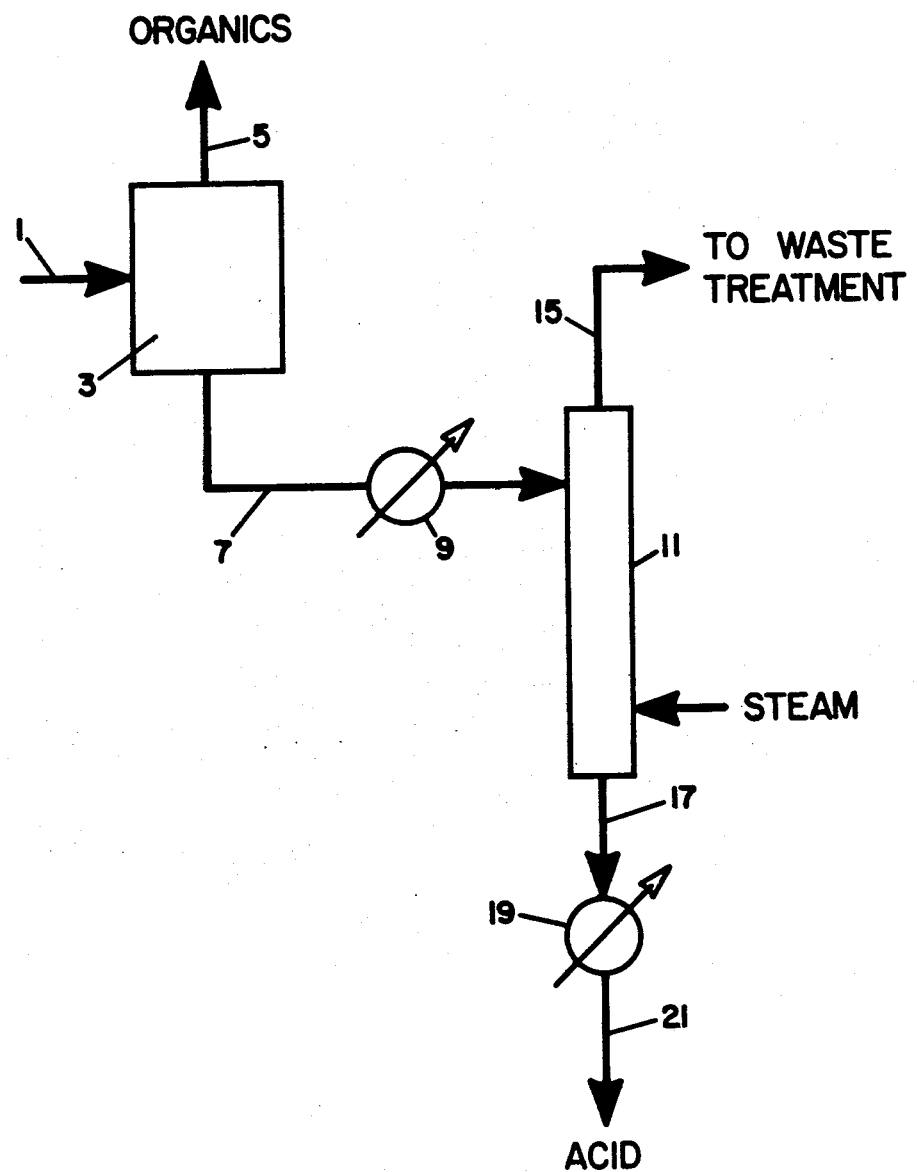

TREATMENT OF CONTAMINATED PHOSPHORIC ACID TO RECOVER USABLE ACID THEREFROM

BACKGROUND AND PRIOR ART

This invention relates to the treatment of phosphoric acid streams recovered from chemical processes, in which such streams contain waste organic materials, particularly sulfur-containing organic materials, to recover the phosphoric acid in usable form, and to eliminate or minimize waste disposal treatment of such acid streams.

One source of phosphoric acid contaminated in such manner is processes for production of aromatic thiols such as thiophenol, ring-substituted thiophenols and naphthalenethiols, by reaction of aromatic sulfonic acids with elemental phosphorus.

Such processes are described, for instance, in U.S. Pat. Nos. 2,947,788 and 3,732,969 of Harold Pitt. In these, an aromatic sulfonic acid such as benzenesulfonic acid is reacted with elemental phosphorus in a first stage to produce an aromatic disulfide and phosphorus acid. In the second stage, the aromatic disulfide is reacted with additional elemental phosphorus and water (with the phosphorous acid usually still present) to produce the aromatic thiol and phosphoric acid. Iodine or iodine-containing materials are employed as catalysts. The aromatic thiol is recovered from the reaction mixture by steam distillation.

The phosphoric acid remaining after steam distillation contains a number of impurities resulting from the overall process. These include organic sulfur compounds such as unreacted aromatic sulfonic acids, aromatic disulfides, aromatic sulfones and other sulfur-containing by-products, and also iodine and/or hydrogen iodide (from the catalyst utilized in the process). In general, the phosphoric acid stream contains at least several percent of such impurities and is not satisfactory for commercial use. It must therefore be disposed of as waste, for instance by deposit in landfills. Such disposal has become undesirable and in addition results in a loss of potentially valuable product.

Another source of such contaminated phosphoric acid lies in processes for production of sulfur-containing organophosphorus acids and esters such as thio-, dithio-, and trithiophosphates, phosphonates, chloridophosphates and phosphonates, etc. These substances, which are useful as intermediates in production of materials such as pesticides, flame retardants, and materials for oil recovery, may be produced by a number of methods such as reaction of various phosphorus sulfides with oxygenated compounds (e.g. alcohols). In such processes, waste streams may be produced, for instance, in distillation, which contain phosphoric acid contaminated with various sulfur-containing substances.

Other sources for such phosphoric acid streams may include processes in which phosphorus compounds such as phosphorus trichloride, phosphorus pentachloride or phosphorus oxychloride ($POCl_3$) are used as reactants or catalysts.

Recovery of phosphoric acid from such processes may be desirable for economic or environmental reasons.

SUMMARY OF THE INVENTION

In general this invention comprises a process for the treatment of phosphoric acid containing organic contaminants which are substantially insoluble in phosphoric acid, comprising:

(a) maintaining the contaminated phosphoric acid at a temperature of from about 80° to about 180° C. for a time sufficient to permit separation into an acidic phase comprising phosphoric acid and an organic phase comprising the major portion of the organic contaminants;

(b) withdrawing the organic phase from contact with the acidic phase;

(c) heating the acidic phase to a temperature sufficient to produce a phosphoric acid concentration of at least about 85%;

(d) stripping the acidic phase from step (c) with steam to remove malodorus organic contaminants; and (e) removing remaining organic contaminents from the stripped acid phase of step (d).

DESCRIPTION OF THE DRAWING

The FIGURE represents a block flow diagram illustrating the conduct of a process according to this invention.

DETAILED DESCRIPTION OF THE INVENTION

This invention is applicable to the treatment of phosphoric acid streams which contain phosphoric acid-insoluble organic contaminents, and particularly organic sulfur contaminents resulting from a number of processes such as those mentioned above.

The organic contaminents which may be removed by this process are those which are substantially insoluble in phosphoric acid, or aqueous phosphoric acid solutions. They include organic sulfur-containing materials such as mentioned elsewhere herein, and/or other organics such as aromatic hydrocarbons (e.g., benzene, toluene, naphthalene, etc.) and substituted aromatic hydrocarbons such as chlorobenzene. These substances may be present as a result of their use as reactants or solvents in the process from which phosphoric acid is recovered.

The process of this invention is particularly appropriate for treating phosphoric acid recovered from a process for production of aromatic thiols, such as thiophenol, which contains organic sulfur contaminants such as aromatic sulfonic acids, aromatic sulfones, aromatic disulfides, and other organic sulfur contaminents, and which may also contain iodine-containing materials such as elemental iodine or hydrogen iodine. The term "aromatic thiols" includes thiophenol, substituted thiophenols such as p-chloro-, methyl-, and 2,4,5-trichloro-phenols, α- or β-naphthalenethiols, and similarly substituted naphthalenethiols. For purposes of convenience, the process according to this invention will be described with relation to such phosphoric acid streams.

A phosphoric acid stream is fed to the process in line 1. When such stream is produced in a thiophenol or other aromatic thiol process, it is generally recovered from the bottom of a steam distillation column or columns employed to separate the desired aromatic thiol product from the phosphoric acid, as mentioned previously. In such case, the stream will generally be at a temperature of about 160°–170° C.

The phosphoric acid stream in line 1 is introduced into a separation apparatus 3 which is maintained at a temperature of at least about 80° C., and generally up to a maximum of about 180° C. Preferably the temperature is from about 120° to about 160° C. In apparatus 3 separation occurs into acidic and organic phases. At temperatures above 80° C. the phases are clear and separate easily due to density differences. The time required for good phase separation depends on the temperatures employed. At lower temperatures up to 20 minutes may be advisable, while at higher temperatures the separation occurs more rapidly.

Separation apparatus 3 may be a decanter, preferably a natural decanter, from which the two phases flow by gravity, or a separation tank with appropriate instrumentation and flow controls.

The organic phase forms in the upper portion of the separation apparatus. It comprises organic sulfur compounds including sulfones, disulfides, thiols and others, and contains the major portion of such contaminants which were present in the phosphoric acid stream fed in line 1. The organic stream is removed from separation tank 3 in line 5 and may be passed to waste disposal. In a preferred embodiment of this invention however, the organic sulfur contaminants contained in line 5 are advantageously used by introducing them into a sulfuric acid regeneration process in which sulfuric acid is obtained from wastes containing sulfur values by high temperature combustion to produce sulfur dioxide which is subsequently oxidized to sulfur trioxide. The sulfur trioxide may be recovered as such, for use in chemical processes or oil recovery, or may be converted to sulfuric acid.

The acidic phase in the lower portion of separation apparatus 3 is removed in line 7. This phase comprises primarily phosphoric acid and will also contain water, aromatic sulfonic acid, aromatic sulfone, iodine and/or hydrogen iodine, and may contain small amounts of other organic sulfur contaminants.

The acidic phase is heated in pre-heater 9 to its bubble point. If the acidic phase contains less than 85% phosphoric acid, the preheating is conducted so as to raise the concentration to at least 85% in order to effect removal of hydrogen iodide in the subsequent stripping step. Generally, for the steam stripping step, the acidic phase must be preheated to at least about 140° C., preferably at least about 150° C. at atmospheric pressure. If the process is operated under vacuum, the preheating temperature will be lower, depending on the operating pressure. Pressures above atmospheric may be employed if necessary or desirable.

The thus heated stream is introduced into a countercurrent steam stripper 11 fed at its lower portion by steam line 13. The stripper 11 will contain appropriate packing, such as rings, and is preferably externally heated with low pressure steam so as to prevent heat losses and condensation in the column.

The overhead product of the column is removed in line 15 and contains, in addition to water, the hydrogen iodide/iodine, malodorous organic sulfur contaminants and any other volatile impurities which may be present. This stream is generally passed to conventional waste treatment facilities (not shown), but may be appropriately treated to recover the hydrogen iodide or iodine in a usable form, if desired. If the stream does not contain any iodine substances, the stripper will function to remove whatever volatiles may be present.

The stripped acid recovered from the lower portion of the column in line 17 contains primarily phosphoric acid and water, together with benzenesulfonic acid, diphenyl sulfone, and minor traces of other contaminants. The acid is generally passed through a cooler 19 in which the acid is cooled sufficiently (e.g. to about 30°–40° C.) to precipitate crystals of diphenyl sulfone, which are removed by filtration. The diphenyl sulfone can be dissolved in the organic layer recovered in line 5, disposed of as solid waste, or purified and marketed as a product. The phosphoric acid recovered from this step in line 21 has been freed of undesirable sulfur contaminants and hydrogen iodide, and is of sufficiently high quality (with optional dilution) to be utilized for industrial purposes such as the manufacture of ammonium phosphate fertilizer.

In general, the process of this invention may be carried out in either batch or continuous manner, as desired. If the capacity of the separation apparatus 3 is large in comparison with the volume of contaminated acid to be treated, the acid stream may be permitted to flow into apparatus 3 until a sufficient volume has been accumulated to warrent drawing off one or both phases. Similarly, the organic phase, which is usually initially much smaller in volume than the acid phase, may be allowed to build up while the acid phase is withdrawn, batchwise or continuously. The material in apparatus 3 may, therefore, be at times as high as 90% organic phase and as low as 10% acidic phase, especially if the acid phase is regularly drawn off.

The acidic phase need not be introduced directly into the steam stripper, but may be stored as convenient, then preheated and stripped.

The hot separation of the organic acid layer, together with steam stripping of iodine content and malodorous sulfur compounds, enables the production of phosphoric acid of commercially utilizable quality, whereas in previously operated processes the phosphoric acid would only be disposed of as waste. As pointed out above, the organic sulfur contaminants may also find value as feed to a sulfuric acid regeneration process, so that overall waste disposal from an aromatic thiol process can be substantially reduced.

EXAMPLE

The following represents an example of the conduct of a process according to this invention, with reference to the FIGURE.

A phosphoric acid stream obtained from a steam distillation column for removal of thiophenol from phosphoric acid is introduced into the process in line 1, at a temperature of about 160°–170° C. The stream has the following approximate composition (in pounds of material per hour):

| | |
|---|---|
| diphenyl sulfone | 64 |
| water | 242 |
| benzenesulfonic acid | 54 |
| thiophenol | trace |
| diphenyl disulfide complex | trace |
| other organics | 160 |
| phosphoric acid | 2,010 |
| hydrogen iodide | 3. |

The separation is conducted in separation tank 3 at the temperature of the phosphoric acid stream, into acidic and organic phases.

The organic phase is removed in line 5 and has the following approximate composition (in pounds per hour):

| | |
|---|---|
| diphenyl sulfone | 40 |
| diphenyl disulfide complex | trace |
| thiophenol | trace |

-continued

|  |  |
|---|---|
| other organics | 160. |

The organic phase is removed in line 5 for further treatment (not shown). As mentioned above, this material may be suitable for introduction into a furnace for regeneration of sulfuric acid from waste materials containing sulfur values. Such regeneration processes may require the phosphorus content of the sulfur feed to be less than 1,000 ppm. The organic sulfur phase removed in line 5 easily meets this specification.

The acidic phase is removed from the separation tank in line 7 and has the following approximate composition (in pounds per hour):

|  |  |
|---|---|
| diphenyl sulfone | 24 |
| water | 242 |
| benzenesulfonic acid | 54 |
| thiophenol | trace |
| diphenyl disulfide complex | trace |
| other organics | trace |
| phosphoric acid | 2,010 |
| hydrogen iodide | 3. |

The acidic stream is then passed through a pre-heater 9 which is operated so as to control the acid at the boiling point of 86% phosphoric acid, or about 160° C. at atmospheric pressure. The preheated stream is than passed into steam stripping column 11 and countercurrently contacted with stripping steam introduced through line 13 at a rate of 0.1 pound of steam per pound of acid. The column employs 8–9 equilibrium stages. In the stripping column, hydrogen iodide, malodorous organic sulfur compounds and miscellaneous light boilers are removed from the acidic phase as overhead in line 15, and passed to conventional waste treatment (not shown).

Recovered from the bottom of the stripping column 11, in line 17, is an acidic stream which contains approximately (pounds of material per hour):

|  |  |
|---|---|
| diphenyl sulfone | 24 |
| water | 242 |
| benzenesulfonic acid | 54 |
| thiophenol | trace |
| diphenyl disulfide complex | trace |
| other organics | trace |
| hydrogen iodide | trace |
| phosphoric acid | 2,010 |

This stream is passed through a cooler 19 which is operated at a temperature of 30°–40° C. so as to precipitate out crystals of diphenyl sulfone. The acid is recovered in line 21, is diluted with water to a strength of approximately 70–75%, and the crystals filtered out. The acid thus produced is suitable for conversion to ammonium phosphate fertilizer.

What is claimed is:

1. A process for the treatment of phosphoric acid containing organic contaminants which are substantially insoluble in phosphoric acid, to recover phosphoric acid therefrom, comprising:
   (a) maintaining the contaminated phosphoric acid at a temperature of from 80° to about 180° C. for a time sufficient to permit separation into an acidic phase comprising phosphoric acid and an organic phase comprising the major portion of the organic contaminants;
   (b) withdrawing the organic phase from contact with the acidic phase;
   (c) heating the acidic phase to a temperature sufficient to produce a phosphoric acid concentration of at least 85%; and
   (d) stripping the acidic phase from step (c) with steam to remove malodorous organic contaminants.

2. A process according to claim 1 in which the phosphoric acid additionally contains hydrogen iodide and/or iodine as a contaminant, which is removed from the phosphoric acid in stripping step (d).

3. A process according to claim 1 in which the organic contaminants comprise organic sulfur-containing substances.

4. A process according to claim 1 in which the organic phase from step (b) is utilized as feed to a sulfuric acid regeneration process.

5. A process according to claim 1 in which the phosphoric acid is obtained from a process for production of an aromatic thiol by reaction of an aromatic sulfonic acid with elemental phosphorus and water.

6. A process according to claim 5 in which the phosphoric acid is obtained from a process for production of aromatic thiols employing an iodine-containing catalyst.

7. A process according to claim 5 in which the aromatic thiol is thiophenol, and the organic sulfur contaminants in the phosphoric acid comprise diphenyl sulfone, diphenyl sulfides, benzenesulfonic acid and thiophenyl.

8. A process according to claim 1 further comprising removing remaining organic contaminants from the stripped acid phase of step (d).

* * * * *